(12) United States Patent
Fu

(10) Patent No.: US 9,486,154 B2
(45) Date of Patent: Nov. 8, 2016

(54) DEVICE AND METHOD FOR RECORDING PHYSIOLOGICAL SIGNAL

(71) Applicant: MediaTek Inc., Hsin-Chu (TW)

(72) Inventor: Chih-Ming Fu, Hsinchu (TW)

(73) Assignee: MEDIATEK INC., Hsin-Chu (TW)

( * ) Notice: Subject to any disclaimer, the term of this patent is extended or adjusted under 35 U.S.C. 154(b) by 0 days.

(21) Appl. No.: 14/460,789

(22) Filed: Aug. 15, 2014

(65) Prior Publication Data

US 2016/0045122 A1 Feb. 18, 2016

(51) Int. Cl.
| | |
|---|---|
| *A61B 5/04* | (2006.01) |
| *A61B 5/046* | (2006.01) |
| *A61B 5/0468* | (2006.01) |
| *A61B 5/0472* | (2006.01) |
| *A61B 5/0464* | (2006.01) |
| *A61B 5/00* | (2006.01) |
| *A61B 5/0452* | (2006.01) |
| *A61N 1/37* | (2006.01) |
| *G06F 19/00* | (2011.01) |

(52) U.S. Cl.
CPC ............ *A61B 5/046* (2013.01); *A61B 5/0022* (2013.01); *A61B 5/04012* (2013.01); *A61B 5/0452* (2013.01); *A61B 5/0464* (2013.01); *A61B 5/0468* (2013.01); *A61B 5/0472* (2013.01); *A61B 5/7221* (2013.01); *A61B 5/7282* (2013.01); *A61B 5/742* (2013.01); *A61B 5/7405* (2013.01); *A61N 1/3702* (2013.01); *A61B 5/0002* (2013.01); *G06F 19/3406* (2013.01)

(58) Field of Classification Search
None
See application file for complete search history.

(56) References Cited

U.S. PATENT DOCUMENTS

| | | | | |
|---|---|---|---|---|
| 4,295,474 | A * | 10/1981 | Fischell | ............... A61B 5/0432 600/510 |
| 2007/0250127 | A1 | 10/2007 | Stylos et al. | |
| 2008/0235469 | A1 * | 9/2008 | Drew | ................ A61B 5/02055 711/159 |
| 2009/0326350 | A1 | 12/2009 | Kracker | |
| 2013/0027186 | A1 * | 1/2013 | Cinbis et al. | ................ 340/10.1 |
| 2013/0267791 | A1 * | 10/2013 | Halperin et al. | .............. 600/300 |
| 2014/0136585 | A1 * | 5/2014 | Brockway | .......... H03H 17/0248 708/317 |

FOREIGN PATENT DOCUMENTS

| | | |
|---|---|---|
| EP | 2015211 A1 | 1/2009 |
| WO | 2006039694 A2 | 4/2006 |

* cited by examiner

*Primary Examiner* — Brian T Gedeon
*Assistant Examiner* — Ankit D Tejani
(74) *Attorney, Agent, or Firm* — McClure, Qualey & Rodack, LLP

(57) ABSTRACT

An apparatus for recording physiological signal is provided. The apparatus includes a storage unit, a signal analyzer, and a controller. The storage unit is configured for storing a physiological signal of a user during a time interval. The signal analyzer is configured for analyzing the physiological signal of the user to provide an analysis result. The controller is configured for changing the time interval according to the analysis result.

20 Claims, 4 Drawing Sheets

DEVICE AND METHOD FOR RECORDING PHYSIOLOGICAL SIGNAL

BACKGROUND OF THE INVENTION

1. Field of the Invention

The invention relates to an apparatus for recording a physiological signal, and more particularly to an apparatus for recording a physiological signal during a variable storing interval.

2. Description of the Related Art

Currently, the measurement of various physiological parameters of a patient is primarily performed at a health center or medical station. Increasingly, the patients can independently use portable medical apparatus to perform such measurements at home. In general, a user only needs to perform simple and easy steps with the portable medical apparatus to complete the measurements. In a mobile measurement mode, the portable medical apparatus will communicate with a remote server by wireless communication, such as Internet or other transmission technology, to transmit data regarding the measurements to a remote server and then obtain a response from the remote server to aid in medical management.

For example, blood pressure can be measured at home with an electronic sphygmomanometer, and body temperature can be measured at home with a clinical thermometer. Next, measurement data is transmitted to a medical center or the like via a communication network. Next, the data is analyzed by a medical expert. Thus, daily health care at home can be performed under the guidance of an expert, providing reliable health care service.

BRIEF SUMMARY OF THE INVENTION

An apparatus and a method for recording physiological signals are provided. An embodiment of an apparatus for recording physiological signal is provided. The apparatus comprises a storage unit, a signal analyzer and a controller. The storage unit is configured for storing a physiological signal of a user during a time interval. The signal analyzer is configured for analyzing the physiological signal of the user to provide an analysis result. The controller is configured for changing the time interval according to the analysis result.

Furthermore, an embodiment of a method for recording physiological signal is provided. A physiological signal of a user is stored during a time interval. The physiological signal of the user is analyzed to provide an analysis result. The time interval is changed according to the analysis result.

A detailed description is given in the following embodiments with reference to the accompanying drawings.

BRIEF DESCRIPTION OF DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
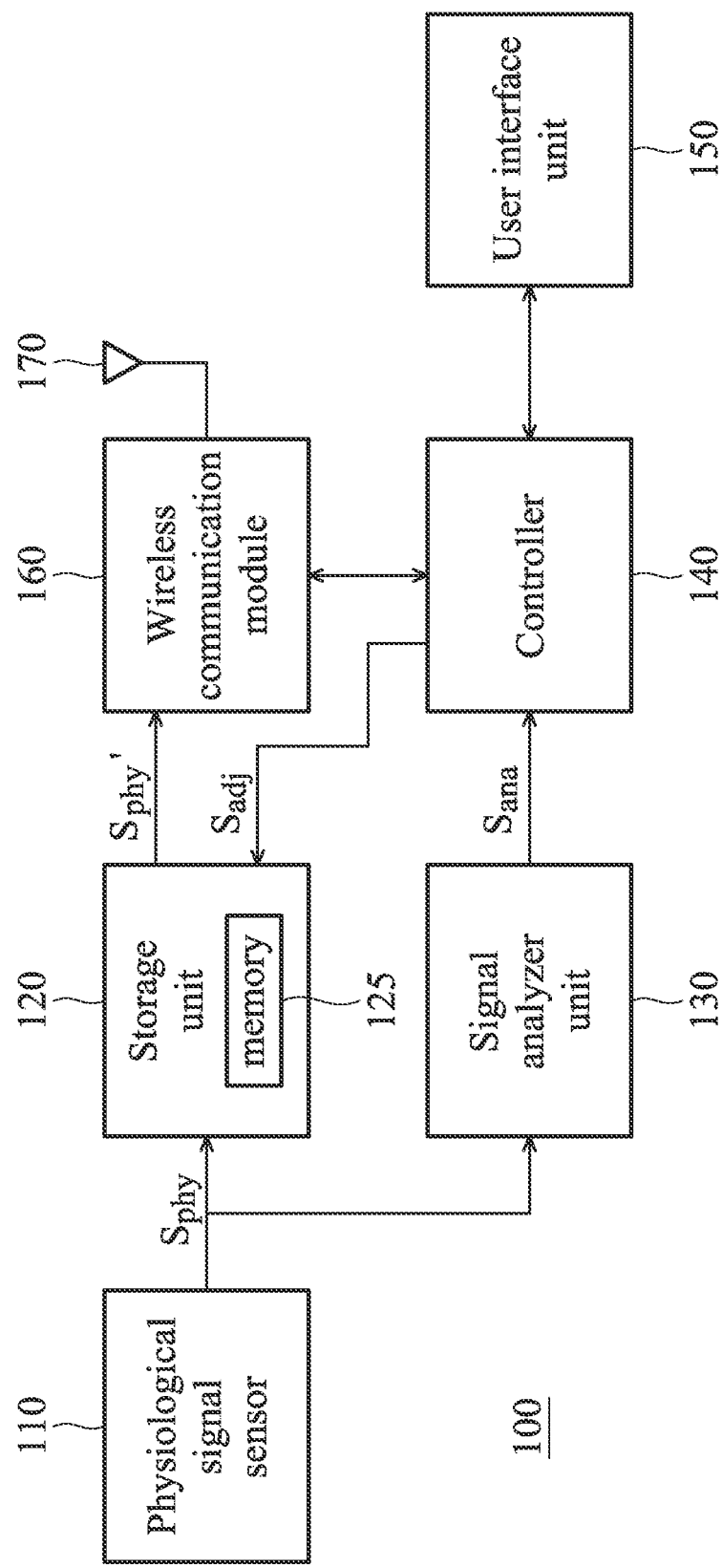
FIG. 1 shows an apparatus for recording a physiological signal according to an embodiment of the invention.

FIG. 1 shows an apparatus 100 for recording a physiological signal according to an embodiment of the invention. In the embodiment, the physiological signal may be user health related information of electrocardiogram (ECG), Electromyography (EMG), electrooculography (EOG), electrogastrography (EGG), electroencephalography (EEG), blood pressure, body temperature and so on. The apparatus 100 comprises a physiological signal sensor 110, a storage unit 120, a signal analyzer 130, a controller 140, a user interface unit 150, a wireless communication module 160 and an antenna 170. When the apparatus 100 is attached correctly to a user, the physiological signal sensor 110 is capable of sensing an aspect of the physiological condition of the user and obtaining a physiological signal $S_{phy}$. In the apparatus 100, the physiological signal $S_{phy}$ may be simultaneously provided to the storage unit 120 and the signal analyzer 130. The storage unit 120 may comprise a memory 125 for storing the physiological signal $S_{phy}$ during a time interval $T_{store}$ to get a stored signal $S_{phy}'$. In the embodiment, the time interval $T_{store}$ is changeable and can be controlled by an adjustment signal $S_{adj}$ from the controller 140. During a term of physiological signal recording, while the storage unit 120 is storing the physiological signal Sphy, the signal analyzer 130 also receives the physiological signal $S_{phy}$ from the physiological signal sensor 110 and analyzes the physiological signal $S_{phy}$ to provide an analysis result $S_{ana}$. Next, the controller 140 changes the time interval according to the analysis result $S_{ana}$ so that the time interval may be increased for the term of physiological signal recording. In this embodiment, the adjustment signal $S_{adj}$ may be sent from the controller 140 to notify the storage unit 120 for increasing the time interval by a specific amount.

In one embodiment, regardless of whether the adjustment is performed, the length of the time interval Tstore is within a predetermined time, e.g. one minute. In FIG. 1, the user interface unit 150 may be a touch panel, which is configured to receive a user input or to output a message (e.g. displaying information about the analysis result Sana) for the user. In one embodiment, the user input may be a health condition or a service request entered by the user. The health condition may carry information of the physical feeling of the user such as pain in the chest and numbness of the hands, which is entered by the user. The service request may notify medical staffs in a remote site to contact the user with a phone call immediately. When obtaining the user input via the user interface unit 150, the wireless communication module 160 may send the user input and the stored physiological signal Sphy' to a remote server for further analysis by doctors. Furthermore, the controller 140 informs the user about the analysis result Sana via the user interface unit 150. In FIG. 1, the controller 140 controls the wireless communication module 160 to transmit the physiological signal Sphy' stored by the storage unit 120 during the time interval Tstore or the user input received by the user interface unit 150 to a remote device, system or server via the antenna 170. Thus, the remote device, system or server can provide responses corresponding to the physiological signal Sphy or the user input to the apparatus 100. After receiving the responses via the antenna 170 and the wireless communication module 160, the controller 140 may display information regarding the responses via the user interface unit, so as to inform the user. In one embodiment, the controller 140 can obtain an instruction from the remote device, system or server via the antenna 170 and the wireless communication module 160, and then the controller 140 can provide the adjustment signal Sadj to the storage unit 120 further according to the instruction, so as to extend the time interval Tstore for collecting more of the physiological signal Sphy. In another embodiment, when the analysis result Sana indicates the physiological signal Sphy is severely abnormal, the controller 140 can use the wireless communication module 160 to facilitate a call service to medical staff via the remote server, so as to provide medical assistance to the user immediately.

To further appreciate FIG. 1, some points are emphasized below. Firstly, the signal analyzer 130 may be a general purpose processor, a digital signal processor (DSP) or the like, which executes some instruction set for analyzing the physiological signal Sphy. However, the signal analyzer 130 may also be implemented by a dedicate hardware. Secondly, in FIG. 1, the physiological signal Sphy are fed both into the storage unit 120 and the signal analyzer 130; in practice, the physiological signal Sphy may be only fed into the storage unit and the signal analyzer 130 can still analyze the physiological signal Sphy by sending request to the storage unit 120. On the contrary, the storage unit 120 may be removed or merged into the signal analyzer 130 by equipping the signal analyzer 130 with a memory unit or input buffer to store the physiological signal Sphy. Also, the controller 140 may be integrated with the signal analyzer 130 as one module to perform both the tasks of analyzing the physiological signal Sphy and changing the time interval. Thirdly, the physiological signal sensor 110 may be a discrete component while the storage unit 120, the signal analyzer 130, the controller 140 and the wireless communication module 160 are fabricated within a integrated circuit (IC). For example, the physiological signal sensor 110 may be a separate ECG signal sensor kit that senses the skin voltages of the user to provide an ECG lead signal and all the other blocks shown in FIG. 1 are components within a mobile phone. The ECG lead signal then may be transmitted to the mobile phone via a wired connection, e.g., universal serial bus (USB) or a wireless connection. Fourthly, aside from the descriptions above, the user interface 150 may also be configured to provide the user information related to the physiological signal recording process such as the analysis result or whether the storing the physiological signal is done. For example, the user interface 150 may serve as an output interface, configured to generate one of a visual signal and an audio signal according to the analysis result. When the analysis result indicates the ECG signal of the user has abnormal morphology, the user interface 150 shows a text message on its display or generates a corresponding audio signal. In addition, the user interface 150 may serve as an output interface, configured to generate a visual signal or an audio signal when the storing the physiological signal of the user is completed. For example, when the storage unit 120 has already stored the physiological signal Sphy for the time interval Tstore, a corresponding sound can be generated to alert the user that the recording of the physiological signal is Sphy done; then the user may detach the physiological signal sensor from his/her body.

Figure 2:
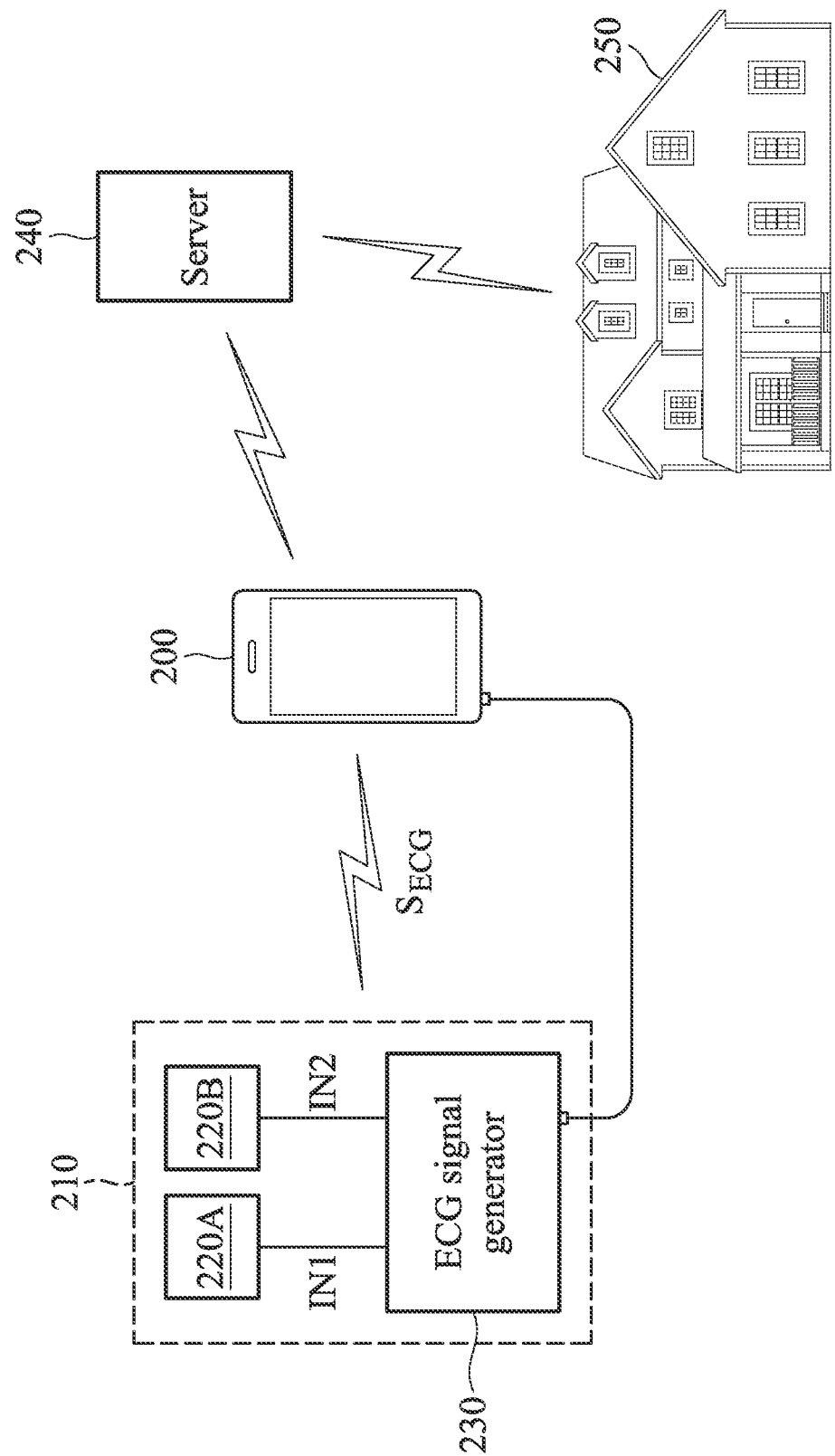
FIG. 2 shows an apparatus for recording a physiological signal according to another embodiment of the invention.

FIG. 2 shows an apparatus 200 for recording a physiological signal according to another embodiment of the invention. In FIG. 2, a physiological signal sensor 210 is an electrocardiogram (ECG) signal sensor, and comprises two electrodes 220A and 220B and an ECG signal generator 230. In general, ECG analysis is a well-established method for analyzing the function of the heart and identifying disorders of the heart. A physiological signal $S_{ECG}$ is a graphic tracing of the variations and the electrical potential caused by the excitation of the heart muscle as detected at the body surface by the physiological signal sensor 210. A normal electrocardiogram is a scale or representation that shows deflections resulting from cardiac activity as changes in the magnitude of voltage and polarity over time and includes a P-Wave, a QRS complex, a T-Wave, and a U-Wave. When the electrodes 220A and 220B are affixed properly to the skin of the user, the ECG signal generator 230 is capable of sensing the physiological condition of the user and obtaining a physiological signal $S_{ECG}$. For example, the ECG signal generator 230 receives a skin voltage signal IN1 from the electrode 220A and a skin voltage signal IN2 from the electrode 220B when the physiological signal sensor 210 is in contact with the skin of the user. The ECG signal generator 230 amplifies a difference between the skin voltage signals IN1 and IN2 to provide a physiological signal $S_{ECG}$. In the embodiment, the electrodes 220A and 220B are used to receive physiological signals from a standard limb lead of the user. Furthermore, the physiological signal sensor 210 can provide the physiological signal $S_{ECG}$ to the apparatus 200 through a wired approach (e.g. a USB connection) or a wireless approach (e.g. Bluetooth (BT), infrared ray and so on). In the embodiment, the apparatus 200 may be a smart phone or a tablet PC. In addition, the physiological signal sensor 210 is separated from the apparatus 200, i.e. the physiological signal sensor 210 is not implemented in the apparatus 100. However, it is also feasible to integrate the physiological signal sensor 210 into the apparatus 200. When obtaining the physiological signal $S_{ECG}$ from the physiological signal sensor 210, a storage unit of the apparatus 200 can store the physiological signal $S_{ECG}$ during a time interval $T_{store}$, and a signal analyzer of the apparatus 200 can analyze the physiological signal $S_{ECG}$ to derive an analysis result. The analysis result may be obtained by using a set of rules and parameters to analyze the P-Wave, the QRS complex, the T-Wave, and the U-Wave of the physiological signal $S_{ECG}$, and then the controller of the apparatus 200 may determine whether to adjust the length of the time interval $T_{store}$ or select the signal time interval to be stored. The controller of the apparatus 200 can change the length of the time interval $T_{store}$ according to the analysis result. In one embodiment, the physiological signal $S_{ECG}$ is stored for 10 seconds, i.e. $T_{store}=10$ s (e.g. default setting). If the apparatus 200 determines that the physiological signal $S_{ECG}$ is reliable according to the characteristic $S_{char}$ of the physiological signal $S_{ECG}$, the apparatus 200 will not change the length of the time interval $T_{store}$, i.e. $T_{store}=10$ s. Conversely, if the apparatus 200 determines that the physiological signal $S_{ECG}$ is unreliable, the apparatus 200 will automatically extend the length of the time interval $T_{store}$, i.e. $T_{store}>10$ s, so as to collect more quantity of the physiological signal $S_{phy}$. Furthermore, the apparatus 200 may transmit the physiological signal $S_{ECG}$ stored during the time interval $T_{store}$ to a hospital 250 (or a medical station, a health center and so on) via a server 240. Thus, a doctor at the hospital 250 can obtain enough information regarding the physiological signal $S_{ECG}$ for diagnosis, and then the doctor of the hospital 250 can provide immediate medical assistance to the user.

Figure 3A:
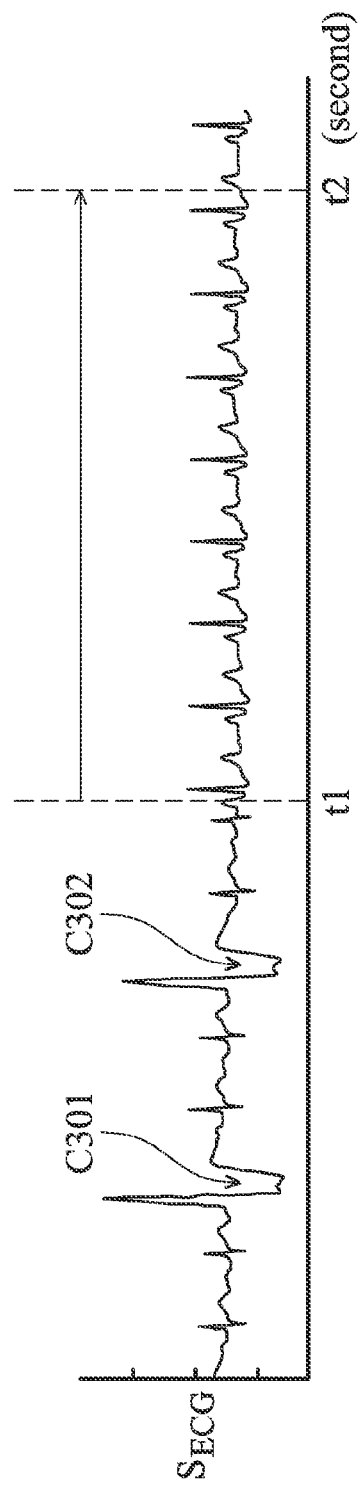
FIG. 3A shows an example illustrating the relationship between the physiological signal of FIG. 2 and a change of the time interval for storing the physiological signal according to an embodiment of the invention.

FIG. 3A shows an example illustrating the relationship between the physiological signal $S_{ECG}$ of FIG. 2 and a change of the time interval $T_{store}$ for storing the physiological signal $S_{ECG}$ according to an embodiment of the invention. Referring to FIG. 2 and FIG. 3A together, the signal analyzer of the apparatus 200 analyzes the physiological signal $S_{ECG}$ of FIG. 3A to derive the analysis result. In the embodiment, the analysis result indicates that the cardiac cycles of the physiological signal $S_{ECG}$ are normal, but waveform variation is inconsistent for some cardiac cycles. Furthermore, the signal analyzer of the apparatus 200 can also analyze a diastolic phase or a systolic phase of some cardiac cycles of the physiological signal $S_{ECG}$ to determine whether the rhythm of the physiological signal $S_{ECG}$ is abnormal. For example, the apparatus 200 usually analyzes five or more cardiac cycles to identify arrhythmia, i.e. the waveforms of the cardiac cycles are the same, but the frequencies of the cardiac cycles are different. In the embodiment, a default length of the time interval $T_{store}$ is from 0 s to time t1. When the morphology of the physiological signal $S_{ECG}$ is abnormal, as shown in label C301, the controller of the apparatus 200 will change the time interval $T_{store}$ at a time instant after C302 but before t1, and then the length of the time interval $T_{store}$ is extended from time t1 to time t2, thereby obtaining a longer sample of the physiological signal $S_{ECG}$ for diagnosis. Thus, a current length of the time interval $T_{store}$ is from 0 s to time t2. In one embodiment, the extended length of the time interval $T_{store}$ is within one minute, i.e. t2<60 s. In another embodiment, when extending length of the time interval $T_{store}$ is performed, changing the time interval increases the time interval by at least 10% of its length before the change, i.e. the time interval is changed by increasing the time interval more than 10%. Furthermore, the apparatus 200 will update the default length of the time interval $T_{store}$ according to the current length of the time interval $T_{store}$. Furthermore, if the apparatus 200 does not need to change the time interval $T_{store}$ in subsequent analyses, the apparatus 200 will keep the length of the time interval $T_{store}$ unchanged (e.g. from 0 s to time t2) or further shorten the length of the time interval $T_{store}$ (e.g. from 0 s to time t1). Furthermore, the current length of the time interval $T_{store}$ will be displayed on the user interface unit of the apparatus 200, so as to notify the user.

Figure 3B:
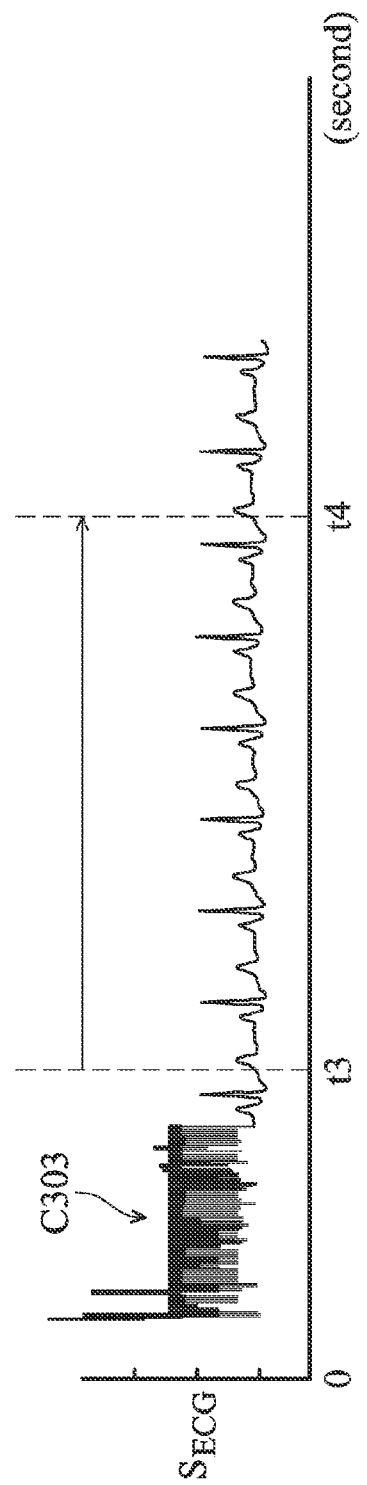
FIG. 3B shows another example illustrating the relationship between the physiological signal of FIG. 2 and a change of the time interval for storing the physiological signal according to another embodiment of the invention.

FIG. 3B shows another example illustrating the relationship between the physiological signal SECG of FIG. 2 and an adjustment of the time interval Tstore for storing the physiological signal SECG according to another embodiment of the invention. Referring to FIG. 2 and FIG. 3B together, the signal analyzer of the apparatus 200 can analyze the physiological signal SECG of FIG. 3B to derive the analysis result. In the embodiment, the analysis result indicates that the physiological signal SECG is noisy, or the physiological signal SECG has a saturation segment (as shows in label C303). Thus, the apparatus 200 may show a message via a display thereof, to notify the user that the electrodes are not attached and need to be pushed tight. Simultaneously, the controller of the apparatus 200 will change the time interval Tstore, and then the length of the time interval Tstore is extended from time t3 to time t4, thereby obtaining more quantity of the physiological signal SECG. Thus, a current length of the time interval Tstore is set from Os to time t4. In one embodiment, the extended length of the time interval Tstore is within one minute, i.e. t4<60 s. Furthermore, if the analysis result indicates that the physiological signal SECG is abnormal morphology, the apparatus 200 will show a message via the display, to notify the user that it is needed to stop recording and change sensing positions of the electrodes. Furthermore, the apparatus 200 will show a message via the display thereof, to require the user to enter a health condition (e.g. pain, palpitation, normal and so on) and a service request (e.g. communication with a doctor). Moreover, the apparatus 200 can send the health condition or the service request to the hospital 250 via the server 240. Next, in response to the health condition or the service request, the hospital 250 can provide an instruction to the apparatus 200 via the server 240 according to the physiological signal SECG, so as to indicate subsequent procedures for the user. Due to the physiological signal SECG stored in the variable time interval Tstore being long enough, the doctor can diagnose immediately without requiring the apparatus 200 to re-record the physiological signal SECG if stored using a fixed time interval.

In brief, adjusting the time interval for storing a physiological signal may be carried out in several approaches and some of them are mentioned below. As an example, the start time or the stop time of the time interval may be changed. For another example, the time interval may be separated into a plurality of intervals and the physiological signal is stored during the plurality of intervals.

Figure 4:
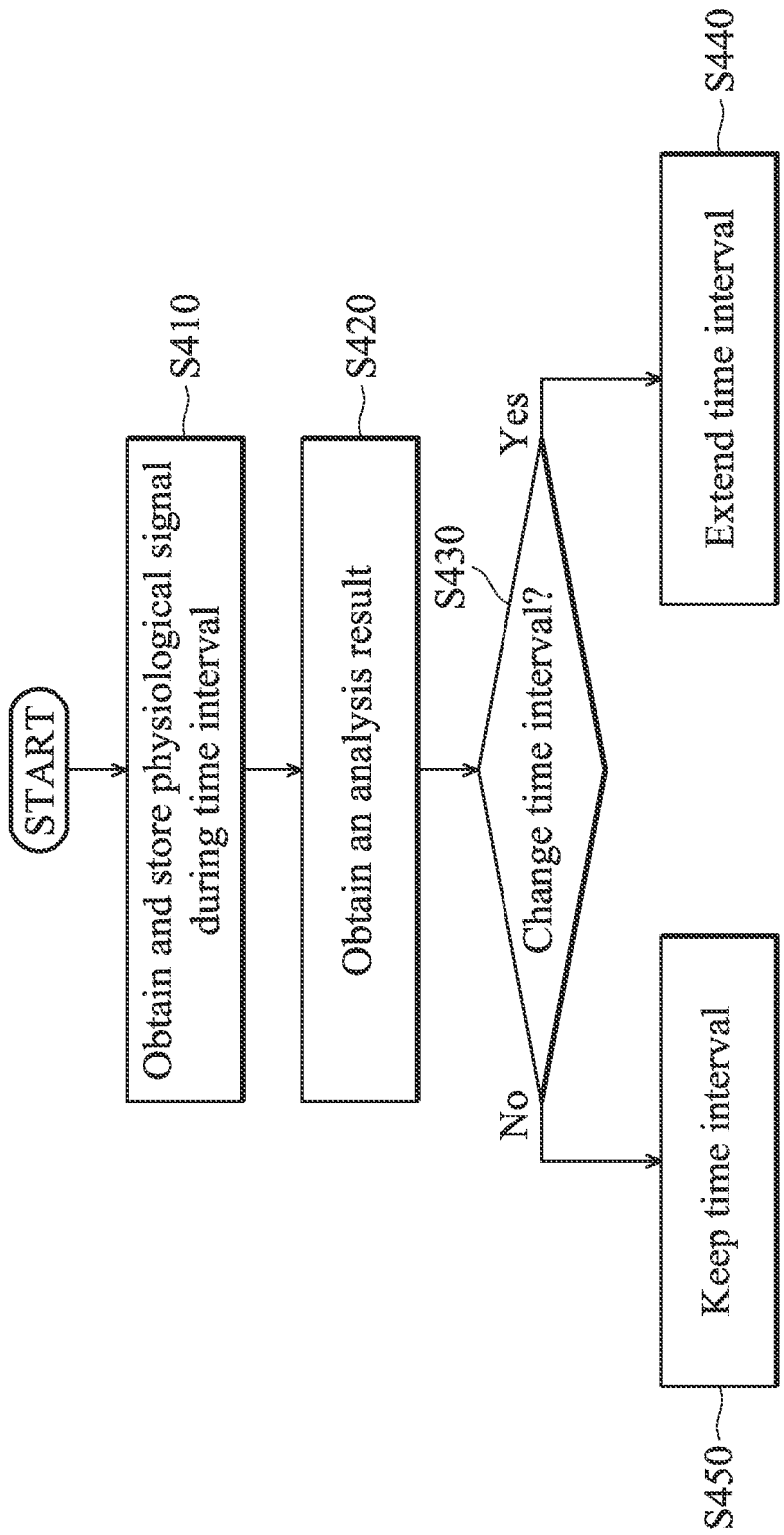
FIG. 4 shows a method for recording a physiological signal according to an embodiment of the invention.

FIG. 4 shows a method for recording a physiological signal (personal health data) according to an embodiment of the invention. In the embodiment, the physiological signal may be user health information regarding electrocardiogram (ECG), Electromyography (EMG), electrooculography (EOG), electrogastrography (EGG), electroencephalography (EEG), blood pressure, body temperature, photoplethysmography (PPG), pulse oximetry (SPO2), non-contact heart rate/beat monitoring, non-contact respiration monitoring, activity graph, and so on. First, in step S410, a physiological signal $S_{phy}$ is obtained and stored/recorded during a time interval $T_{store}$, wherein the time interval is set from a first time point to a second time point. Before reaching the second time point, the obtained physiological signal $S_{phy}$ is analyzed to obtain an analysis result (step S420). In one embodiment, the analysis result comprises information regarding to signal type or quality of the obtained physiological signal $S_{phy}$. In one embodiment, the time interval $T_{store}$ can be divided into a plurality of time periods or segments, and the slope and absolute value of the obtained physiological signal $S_{phy}$ are calculated in each time period, so as to determine whether the obtained physiological signal $S_{phy}$ is saturation, rapid transition, low signal to noise ratio, or flat line in each time period. For example, when the slope of the obtained physiological signal $S_{phy}$ is zero in a specific time period, the analysis result will indicate that the obtained physiological signal $S_{phy}$ is saturation in the specific time period. Next, it is determined whether to change the time interval $T_{store}$ according to the analysis result (step S430). In the embodiment, the analysis result is indicative of whether the physiological signal $S_{phy}$ is unreliable, whether the physiological signal $S_{phy}$ is noisy, whether the morphology of the physiological signal $S_{phy}$ is abnormal, whether the rhythm of the physiological signal $S_{phy}$ is abnormal, or whether the physiological signal $S_{phy}$ is normal. For example, if the physiological signal $S_{phy}$ is unreliable, the length of the time interval $T_{store}$ is extended (step S440), i.e. the time interval $T_{store}$ is set from a first time point to a third time point, wherein the third time point is longer than the second time point. Conversely, if the physiological signal $S_{phy}$ is reliable, the length of the time interval $T_{store}$ is not changed (step S450). In the embodiment, the obtained physiological signal $S_{phy}$ can be checked first, so as to determine whether to extend the time interval $T_{store}$ for collecting more information for the remote server. Thus, diagnosis of the user's status is accurate and efficient when the amount of the physiological signal transmitted to the remote server is sufficient. Furthermore, when the physiological signal $S_{phy}$ obtained in the extended time interval $T_{store}$ is normal, the extended time interval $T_{store}$ can be kept unchanged or shortened.

According to the embodiments, by dynamically adjusting the time interval $T_{store}$ in response to the analysis result, a greater quantity of the physiological signal $S_{phy}$ can be collected automatically. Thus, health state of the user can be immediately diagnosed via the remote server when the quantity of the physiological signal $S_{phy}$ obtained in the variable time interval $T_{store}$ is sufficient.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An apparatus for recording physiological signal, comprising:
    a storage unit, configured for storing a physiological signal of a user during a storing time interval;
    a signal analyzer, configured for analyzing the physiological signal of the user to provide an analysis result; and
    a controller, configured for changing the storing time interval according to the analysis result.

2. The apparatus as claimed in claim 1, wherein the storing time interval is less than 60 seconds, and the controller changes the storing time interval by increasing the storing time interval more than 10%.

3. The apparatus as claimed in claim 1, wherein the storing time interval is changed by changing the start time of the storing time interval, changing the stop time of the storing time interval, or separating the storing time interval into a plurality of intervals.

4. The apparatus as claimed in claim 1, wherein the storage unit receives the physiological signal of the user from a physiological signal sensor through one of a wired connection and a wireless connection.

5. The apparatus as claimed in claim 1, wherein the physiological signal of the user is an electrocardiography (ECG) signal and the analysis result is indicative of one of whether the ECG signal is unreliable, whether the ECG signal is noisy, whether morphology of the ECG signal is abnormal, whether rhythm of the ECG signal is abnormal, and whether the ECG signal is normal.

6. The apparatus as claimed in claim 5, wherein the controller extends the storing time interval when the analysis result is indicative of the morphology of the ECG signal being abnormal or the ECG signal being unreliable.

7. The apparatus as claimed in claim 1, further comprising:
    an input interface configured to receive input information, wherein the input information comprises one of a health condition and a service request entered by the user.

8. The apparatus as claimed in claim 7, further comprising:
    a wireless communication module configured to transmit one of the physiological signal of the user and the input information to a remote server or to establish a connection for an on-line service between a remote server and the user.

9. The apparatus as claimed in claim 1, further comprising:
    an output interface configured to generate one of a visual signal and an audio signal according to the analysis result.

10. The apparatus as claimed in claim 1, further comprising:
    an output interface configured to generate one of a visual signal and an audio signal when the storing the physiological signal of the user is completed.

11. A method for recording physiological signal, comprising:
    storing a physiological signal of a user during a storing time interval;
    analyzing the physiological signal of the user to provide an analysis result; and
    changing the storing time interval according to the analysis result.

12. The method as claimed in claim 11, wherein the storing time interval is less than 60 seconds and the storing time interval is changed by increasing the storing time interval more than 10%.

13. The method as claimed in claim 11, wherein the step of changing the storing time interval further comprises:
    changing the start time of the storing time interval;
    changing the stop time of the storing time interval; or
    separating the storing time interval into a plurality of intervals.

14. The method as claimed in claim 11, wherein the physiological signal of the user is received from a physiological signal sensor through one of a wired connection or a wireless connection.

15. The method as claimed in claim 11, wherein the physiological signal of the user is an electrocardiography (ECG) signal and the analysis result is indicative of one of whether the ECG signal is unreliable, whether the ECG signal is noisy, whether morphology of the ECG signal is abnormal, whether rhythm of the ECG signal is abnormal, and whether the ECG signal is normal.

16. The method as claimed in claim 11, wherein the storing time interval is extended when the analysis result is indicative of the morphology of the ECG signal being abnormal or the ECG signal being unreliable.

17. The method as claimed in claim 11, further comprising:
    transmitting the physiological signal of the user to a remote server.

18. The method as claimed in claim 17, further comprising:
    establishing an on-line service between the remote server and the user.

19. The method as claimed in claim 11, further comprising:
    generating one of a visual signal and an audio signal according to the analysis result.

20. The method as claimed in claim 11, further comprising:
    generating one of a visual signal and an audio signal when the storing the physiological signal of the user is completed.

* * * * *